(12) United States Patent
Kronestedt

(10) Patent No.: US 8,277,412 B2
(45) Date of Patent: Oct. 2, 2012

(54) ONE SHOT INJECTOR WITH DUAL SPRINGS

(75) Inventor: Victor Kronestedt, Stockholm (SE)

(73) Assignee: SHL Group AB, Nacka Strand (SE)

( * ) Notice: Subject to any disclaimer, the term of this patent is extended or adjusted under 35 U.S.C. 154(b) by 114 days.

(21) Appl. No.: 12/666,976

(22) PCT Filed: Jun. 24, 2008

(86) PCT No.: PCT/EP2008/057986
§ 371 (c)(1),
(2), (4) Date: Jun. 15, 2010

(87) PCT Pub. No.: WO2009/007229
PCT Pub. Date: Jan. 15, 2009

(65) Prior Publication Data
US 2010/0249705 A1    Sep. 30, 2010

(30) Foreign Application Priority Data

Jul. 6, 2007 (SE) .................................. 0701647
Aug. 17, 2007 (SE) ................................ 0701896

(51) Int. Cl.
*A61M 5/20* (2006.01)
(52) U.S. Cl. ....................................... 604/134

(58) Field of Classification Search .......... 604/110–111, 604/134–139, 192, 194, 195, 198
See application file for complete search history.

(56) References Cited

U.S. PATENT DOCUMENTS 5,320,609 A * 6/1994 Haber et al. ................. 604/135
6,805,686 B1 * 10/2004 Fathallah et al. ............. 604/135

FOREIGN PATENT DOCUMENTS

| EP | 0577448 A1 | 1/1994 |
| GB | 805184 A | 12/1958 |
| WO | 99/03529 A2 | 1/1999 |
| WO | 99/20327 A2 | 4/1999 |

OTHER PUBLICATIONS

EPO, Int'l Search Report in PCT/EP2008/057986, Oct. 30, 2008.
EPO, Written Opinion in PCT/EP2008/057986, Oct. 30, 2008.

* cited by examiner

*Primary Examiner* — Christopher D Koharski
(74) *Attorney, Agent, or Firm* — Potomac Patent Group PLLC

(57) ABSTRACT

The present invention relates to a medical delivery device comprising a generally elongated housing, a container containing medicament to be delivered, a drive means capable of acting on said container for expelling said medicament, wherein said drive means comprises at least two force spring means arranged between a fixed part of the device and a movable part of the device.

16 Claims, 6 Drawing Sheets

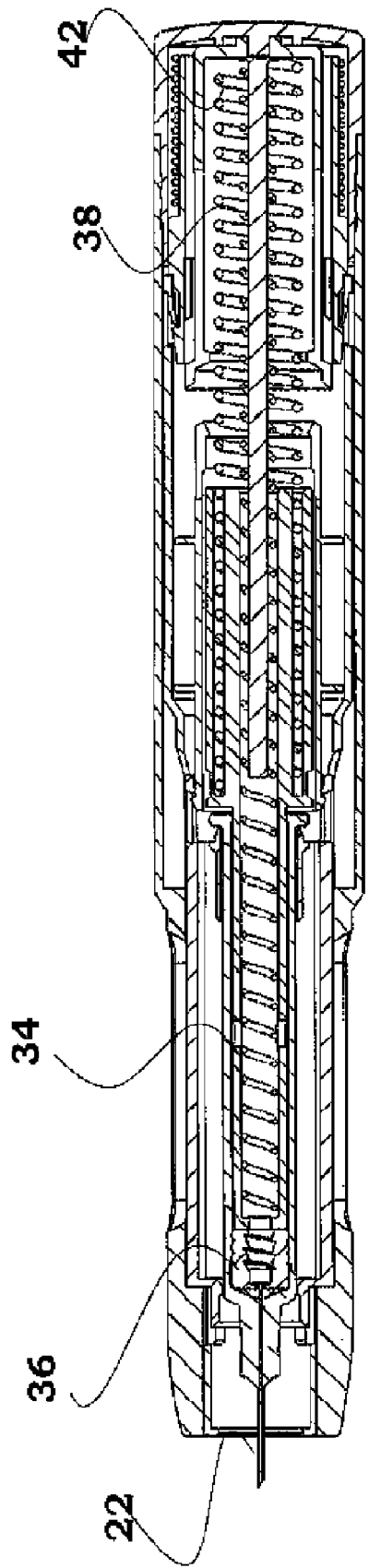
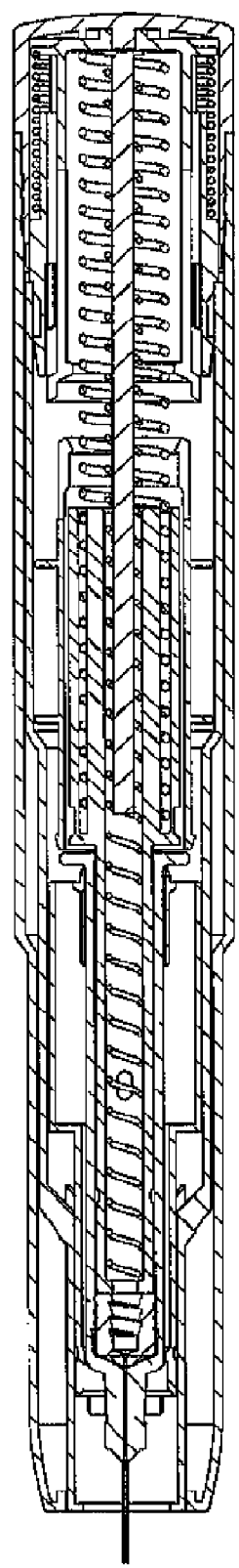
Fig. 5a
Fig. 5b

ONE SHOT INJECTOR WITH DUAL SPRINGS

TECHNICAL FIELD

The present invention relates to an injection device and in particular an injection device capable of handling medicament in fluid form having high viscosity.

BACKGROUND ART

The present invention relates to injection devices for injecting medicament and other types of fluids to be used in for example cosmetic treatment.

This type of drugs often have a high viscosity which means that they require high forces in order to press the fluid through a hollow needle when injecting them.

Auto-injectors having an automated injection function often work with spirally wound compression springs, where the springs act on a plunger rod, which in turn acts on a stopper inside a medicament container, for expelling medicament through an attached needle. The other end of the spring is often abutting an inner end surface of the housing of the device, which means that the housing has to be dimensioned to the forces of the spring.

When handling fluids with high viscosity this becomes even more pronounced because of the high forces required to expel the medicament. Further the spring becomes very large both regarding the diameter of the wound spring and also the diameter of the thread of the wire. The size of the spring means that the device becomes large, and for some applications and customers, such sizes of the devices are not acceptable.

Document WO 9421316 discloses an injection device arranged with two coil springs of different diameter working in concert. The idea of having two springs is to handle the rather long travel of the drive member, which could be difficult with a single spring because of a tendency of buckling when fully compressed and becoming entangled with interior components of the device.

With the dual spring arrangement one spring is arranged between an end plate and the base of an elongated cup. The cup has also an outwardly flange and the second spring acts between this and a wall across the cylindrical drive member.

This design can be used for handling long travel but cannot be utilised when larger forces are required. It is not possible to add the forces of the two springs because of the intermediary cup. The rear spring acts to move the cup forward, and thus the front spring, and then the front spring should act on the drive member. This means that the rear spring has to be so strong that the cup will not be moved backward due to the force of the front spring.

BRIEF DESCRIPTION OF THE INVENTION

The aim of the present invention is to provide an injector being capable of handling the expelling of liquids having high viscosity without increasing the size of the injector in any substantive way.

This aim is obtained with an injector according to the features of claim 1. Preferable embodiments of the invention are the subject of the dependent claims.

According to a main aspect of the invention it is characterised by a medical delivery device comprising a generally elongated housing, a container adapted to contain medicament and a stopper sealingly and slidable arranged inside said container, energy accumulating means, drive means arranged with an outer front end in contact with said stopper, such that, when a force from said energy accumulating means is applied to the drive means, the stopper moves towards the front end of the container and expels the medicament, wherein said energy accumulating means comprises at least two force spring means arranged inside the drive means between inner walls of said driving means and a rear fixed part of the device.

According to another aspect of the invention, said driving means is a tubular plunger rod having at its rear end a tubular enlargement forming a cylindrical space.

According to a further aspect of the invention, one force spring means is arranged inside said tubular plunger rod, and at least a second force spring means is arranged inside said tubular enlargement.

According to yet an aspect of the invention, it further comprises holding means capable of acting on said drive means for holding said at least two force spring means in a loaded state.

According to a further aspect of the invention, it further comprises an actuating means capable of acting on said holding means for releasing said drive means and thereby said at least two loaded force spring means.

According to yet an aspect of the invention, it further comprises a needle shield arranged slidable in said housing capable of acting on said actuating means when said needle shield is pressed against an injection site.

According to yet an aspect of the invention, said actuating means further comprises a resilient means for urging said needle shield towards the front end of the device when said device is removed from the injection site.

The advantages with the present invention are several. Because the device is arranged with at least two spring force means, a large force can be obtained in the device without having to use a very large single spring. The device is thus capable of handling liquid medicament having high viscosity, without the device having to be large and bulky, and thus not very attractive to users.

The size of the device can be kept within reasonable dimensions since preferably one spring force means is arranged inside the plunger rod and a second spring force means is arranged outside the plunger rod.

Also preferably, the injector is arranged with automatic penetration and injection functions, which functions are activated by the needle shield being pressed against an injection site.

These and other aspects of and advantages with the present invention will become apparent from the following detailed description and from the accompanying drawings.

BRIEF DESCRIPTION OF THE DRAWINGS

In the following detailed description of the invention, reference will be made to the accompanying drawings, of which FIGS. 5a-b are cross-sectional view of the injector of FIG. 1 where injection has been completed.

DETAILED DESCRIPTION OF THE INVENTION

Figures 1A, 1B:
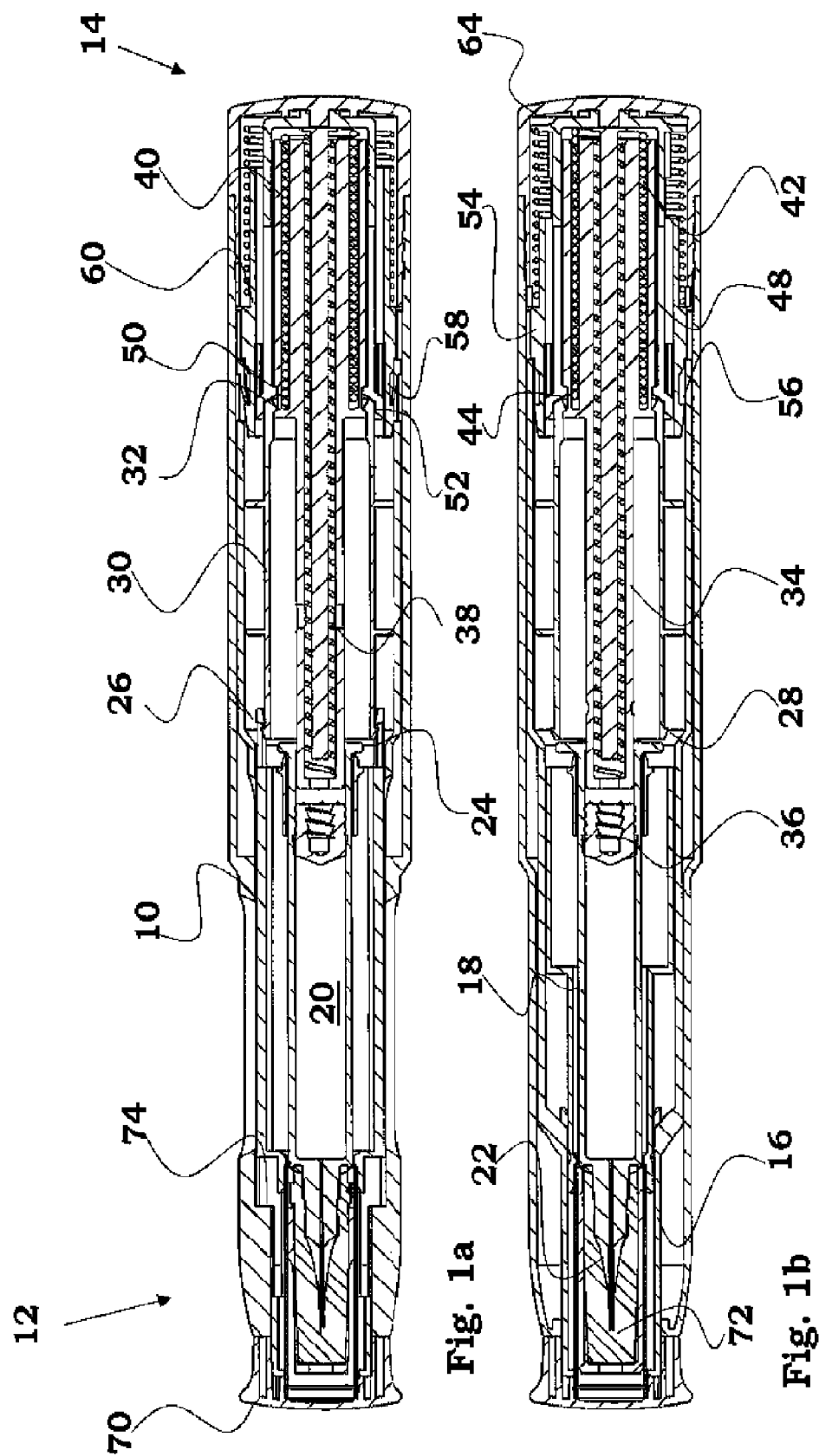
FIGS. 1a-b are cross-sectional views of an injector according to the present invention in a state when delivered to a user, where cross-section b is taken 90° in relation to cross-section a in all the figures.

The embodiment of the injector shown in the drawings comprises an elongated housing 10 with a front end 12, to the left in the figures, which is pressed against the injection site during use, as will be described below, and an opposite rear end 14. At the front end of the housing a generally tubular needle shield 16 is slidably arranged. The rear end of the needle shield extends into the rear part of the housing, in a manner that will be described below.

Inside the needle shield a medicament container holder 18 is arranged, and inside the container holder a container 20, e.g. a cartridge, a syringe or the like, is arranged containing medicament to be delivered through a needle 22 attached to the container.

The rear part of the container holder is arranged with tongues 24 having inwardly directed ledges 26. These ledges cooperate with an outwardly directed circumferential ledge 28 of a generally tubular part 30, creating a snap-on fit between these components. At the rear end of the tubular part an inwardly directed annular ledge 32 is arranged.

Inside the tubular part a drive means 34, e.g. a tubular plunger rod, is arranged with a front end in contact with a stopper 36 in the medicament container. Inside the tubular plunger rod a first energy accumulating means 38, e.g. a first coil drive spring, is arranged between a front end inner wall of the tubular plunger rod and a rear inner wall of the housing. The tubular plunger rod is further arranged with a generally tubular enlargement 40 forming a cylindrical space, in which a second energy accumulating member 42, e.g. a second coil drive spring, is arranged between a front end inner wall of the space and the rear inner wall of the housing. On the outer surface of the tubular enlargement a circumferential groove 44 is arranged.

Outside the tubular enlargement of the plunger rod a generally tubular holding sleeve 46 is arranged. A part of the holding sleeve is arranged with a number of elongated slots whereby arms 48 are formed between the slots. The ends of the arms are arranged with inwardly directed ledges 50 as well as outwardly directed ledges 52.

Outside the holding sleeve an actuator sleeve 54 is arranged, having a diameter somewhat larger than the cross-sectional measure of the arms of the holding sleeve. The actuator sleeve is arranged with a ledge 56 around its circumference and the tongues 58 of the needle shield snap into the space behind the ledges, thereby locking the needle shield to the actuator sleeve. The actuator sleeve is further arranged with a rearwardly facing ledge 60, and a resilient means 62, e.g. a coil spring, is arranged between the ledge and a circumferential ledge 64 of the holding sleeve, thus urging the actuator sleeve and needle shield towards the front of the device.

Figures 2A, 2B:
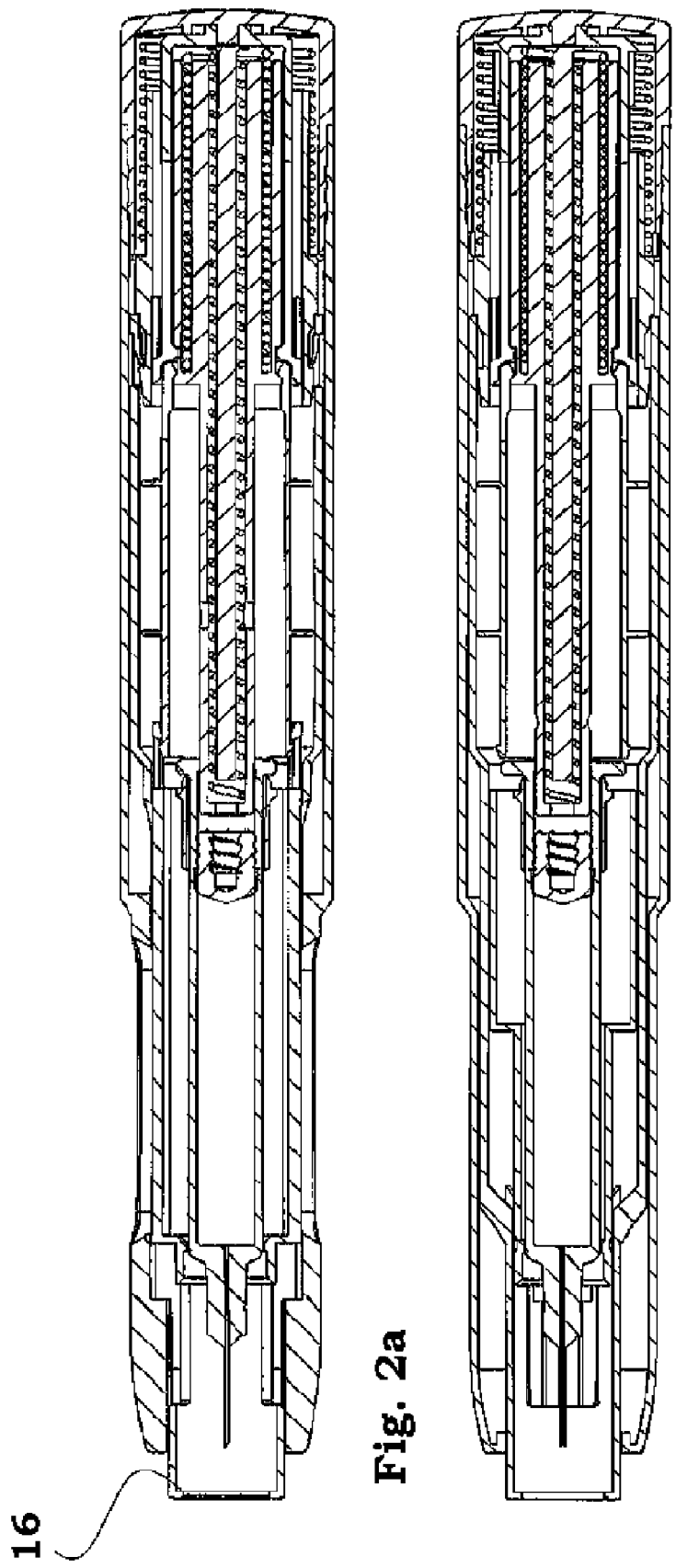
FIGS. 2a-b are cross-sectional views of the injector of FIG. 1 where it is ready for use.

The device is intended to function as follows. When the device is delivered to a user, a protective cap 70 is arranged at the front end of the device. The protective cap comprises a tubular sheath 72 covering the needle in a sterile way. When the cap is removed, so is also the sheath. This also causes the needle shield 14 to move forward and protrude somewhat at the front end of the injector, FIG. 2.

Figure 3A:
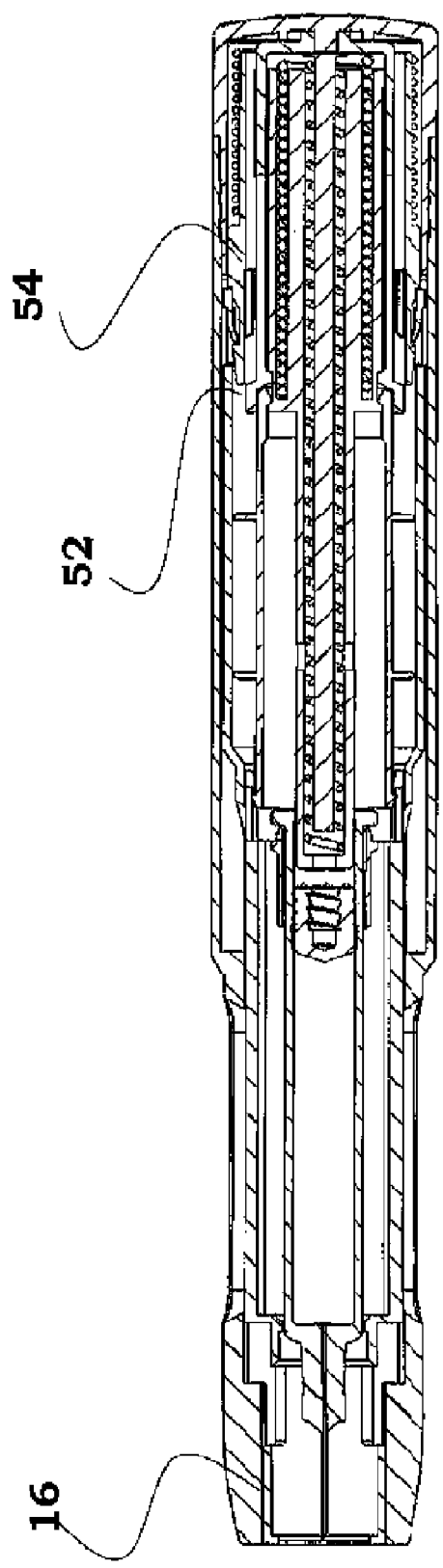
FIGS. 3a-b are cross-sectional view of the injector of FIG. 1 where penetration has been initiated.
Figure 3B:
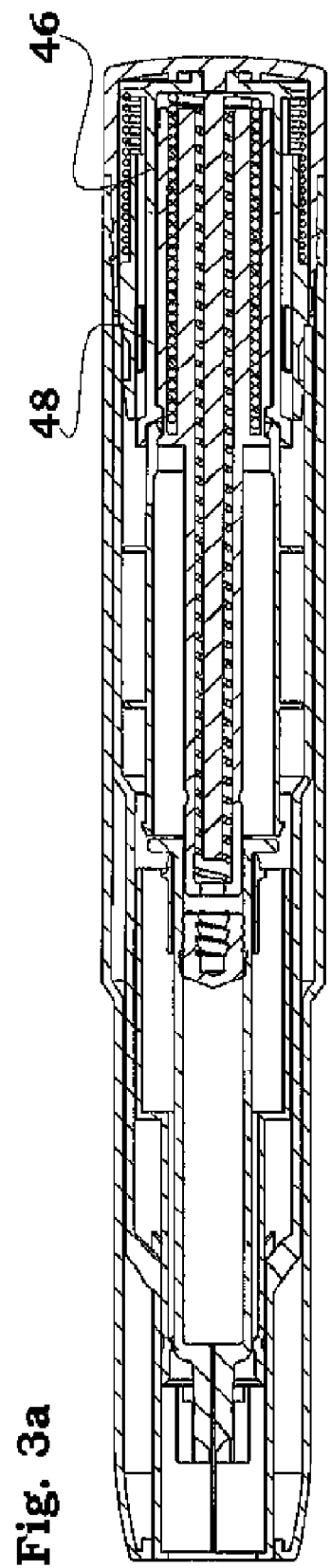

The injector is now ready to use. The front end with the needle shield 16 is pressed against the injection site, whereby the needle shield is pushed into the housing of the device, FIG. 3. Since the needle shield is connected to the actuator sleeve 54, the latter is moved rearwardly in the housing.

Figure 4A:
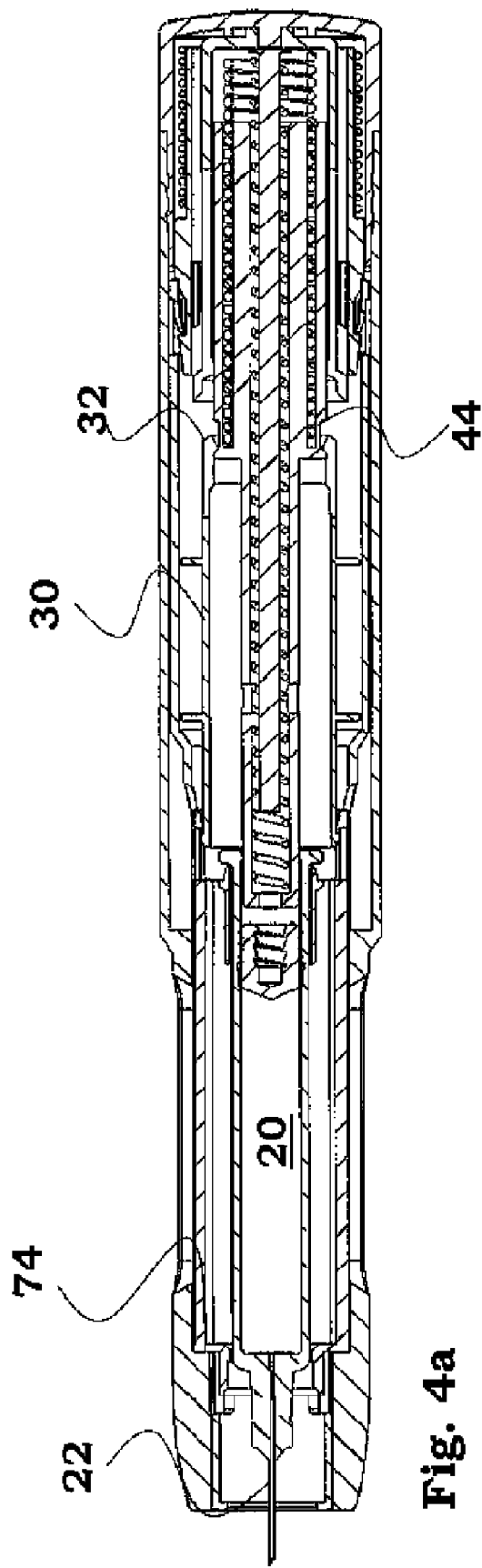
FIGS. 4a-b are cross-sectional view of the injector of FIG. 1 where penetration has been completed.
Figure 4B:
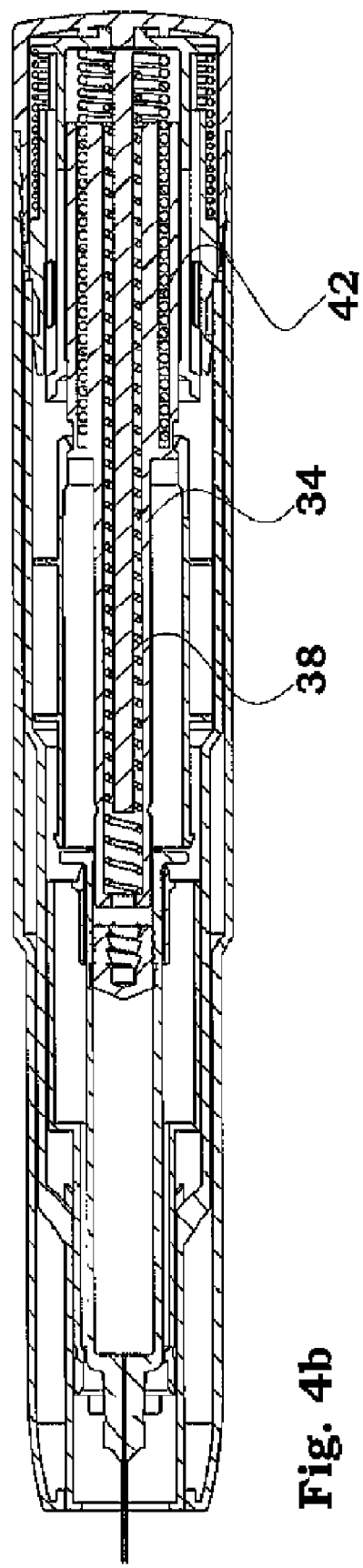

The movement of the actuator sleeve causes it to be moved past the outwardly protruding ledges 52 of the arms 48 of the holder 46. The arms are thus free to flex radially whereby the inwardly directed ledges of the arms are moved out of holding engagement with the groove 44 of the cylindrical part 40 of the tubular plunger rod 34. The tubular plunger rod is now free to move forward due to the forces of the first and second drive springs 38, 42 acting together on the tubular plunger rod. The inwardly directed ledge 32 of the tubular part 30 is still arranged in the groove 44 of the tubular plunger rod, and since the tubular part is connected to the container holder 18, they are moved forward due to the force of the springs, FIG. 4. When the container holder has moved a certain distance, performing the penetration of the needle, it comes in contact with a stop ledge 74 arranged in the housing. The force of the springs will however move the tubular plunger rod further forward, whereby the inwardly directed ledge 32 is moved out of engagement with the annular groove 44 of the tubular plunger rod 34, FIG. 5.

The further movement of the tubular plunger rod 34 moves the stopper 36 inside the medicament container, whereby the pressure from the dual springs 38, 42 will cause the medicament to be pressed through the passage of the needle 22 and to be expelled into the tissue of the patient. The injection is completed when the stopper is at the front end of the container and/or when the front end of the tubular part of the tubular plunger rod comes in contact with the rear end wall of the container.

Figure 6A:
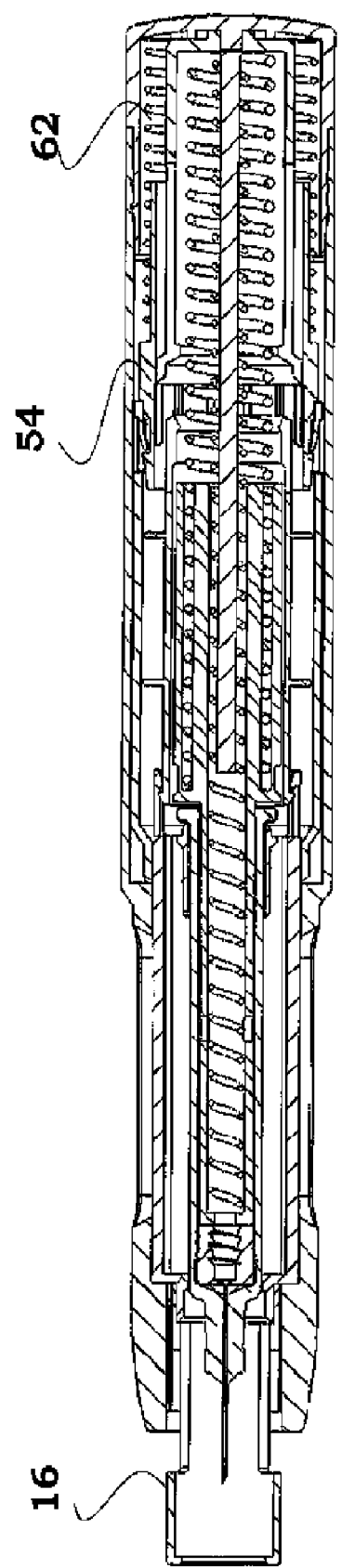
FIGS. 6a-b are cross-sectional view of the injector of FIG. 1 where it has been withdrawn from the injection site.
Figure 6B:
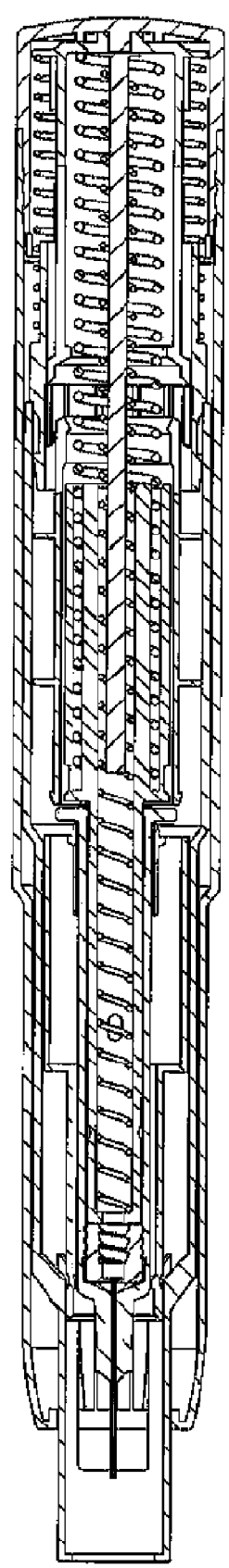

The device may now be removed from the injection site. The spring 62 acting on the actuator sleeve 54 will cause the needle shield 16 to move forward, FIG. 6, since the needle shield is connected to the actuator sleeve, thereby covering the needle. The device is now ready to be discarded.

It is to be understood that the embodiment described above and shown in the drawings is to be regarded only as non-limiting examples of the present invention and that it may be modified within the scope of the patent claims.

The invention claimed is:

1. A medical delivery device, comprising:
    a generally elongated housing;
    a container adapted to contain medicament and a stopper sealingly and slidably arranged inside the container;
    an energy accumulator; and
    a drive mechanism arranged with an outer front end in contact with the stopper, such that, when a force from the energy accumulator is applied to the drive mechanism, the stopper moves toward the front end of the container and expels the medicament;
    wherein the energy accumulator includes at least two force spring devices arranged inside the drive mechanism between inner walls of the driving mechanism and a rear fixed part of the delivery device.

2. The medical delivery device of claim 1, further comprising a holder configured to act on the drive mechanism for holding the at least two force spring devices in a loaded state.

3. The medical delivery device of claim 2, further comprising an actuator configured to act on the holder for releasing the drive mechanism and thereby the at least two loaded force spring devices.

4. The medical delivery device of claim 3, further comprising a needle shield slidably arranged in the housing and configured to act on the actuator when the needle shield is pressed against an injection site.

5. The medical delivery device of claim 4, wherein the actuator comprises a resilient device configured to urge the needle shield toward a front end of the delivery device when the delivery device is removed from the injection site.

6. The medical delivery device of claim 1, wherein the drive mechanism is a tubular plunger rod having at its rear end a tubular enlargement forming a cylindrical space.

7. The medical delivery device of claim 6, further comprising a holder configured to act on the drive mechanism for holding the at least two force spring devices in a loaded state.

8. The medical delivery device of claim 7, further comprising an actuator configured to act on the holder for releasing the drive mechanism and thereby the at least two loaded force spring devices.

9. The medical delivery device of claim 8, further comprising a needle shield slidably arranged in the housing and configured to act on the actuator when the needle shield is pressed against an injection site.

10. The medical delivery device of claim 9, wherein the actuator comprises a resilient device configured to urge the needle shield toward a front end of the delivery device when the delivery device is removed from the injection site.

11. The medical delivery device of claim 6, wherein a first force spring device is arranged inside the tubular plunger rod, and at least a second force spring device is arranged inside the tubular enlargement.

12. The medical delivery device of claim 11, further comprising a holder configured to act on the drive mechanism for holding the at least two force spring devices in a loaded state.

13. The medical delivery device of claim 12, further comprising an actuator configured to act on the holder for releasing the drive mechanism and thereby the at least two loaded force spring devices.

14. The medical delivery device of claim 13, further comprising a needle shield slidably arranged in the housing and configured to act on the actuator when the needle shield is pressed against an injection site.

15. The medical delivery device of claim 14, wherein the actuator comprises a resilient device configured to urge the needle shield toward a front end of the delivery device when the delivery device is removed from the injection site.

16. The medical delivery device of claim 1, wherein the drive mechanism is a tubular plunger rod.

* * * * *